US010689531B2

(12) United States Patent
McJunkins et al.

(10) Patent No.: US 10,689,531 B2
(45) Date of Patent: Jun. 23, 2020

(54) COATING COMPOSITION COMPRISING SUBMICRON CALCIUM CARBONATE-COMPRISING PARTICLES, PROCESS TO PREPARE SAME AND USE OF SUBMICRON CALCIUM CARBONATE-COMPRISING PARTICLES IN COATING COMPOSITIONS (71) Applicant: Omya International AG, Oftringen (CH)

(72) Inventors: Joseph McJunkins, Middleburg Heights, OH (US); Charles Freeman, Rutland, VT (US)

(73) Assignee: Omya International AG, Oftringen (CH)

( * ) Notice: Subject to any disclaimer, the term of this patent is extended or adjusted under 35 U.S.C. 154(b) by 245 days.

(21) Appl. No.: 15/084,766

(22) Filed: Mar. 30, 2016

(65) Prior Publication Data
US 2016/0244621 A1    Aug. 25, 2016

Related U.S. Application Data (62) Division of application No. 13/980,386, filed as application No. PCT/EP2012/053089 on Feb. 23, 2012.

(60) Provisional application No. 61/446,006, filed on Feb. 23, 2011.

(51) Int. Cl.
| | |
|---|---|
| *C09D 7/40* | (2018.01) |
| *C09D 175/06* | (2006.01) |
| *A61K 8/02* | (2006.01) |
| *C09C 1/02* | (2006.01) |
| *B82Y 30/00* | (2011.01) |
| *C08K 3/26* | (2006.01) |
| *C09D 5/02* | (2006.01) |
| *C09D 7/61* | (2018.01) |
| *A61Q 19/00* | (2006.01) |
| *A61K 8/19* | (2006.01) |
| *C08K 3/20* | (2006.01) |
| *A61Q 3/02* | (2006.01) |
| *C09C 3/04* | (2006.01) |
| *C01F 11/18* | (2006.01) |

(52) U.S. Cl.
CPC .............. *C09D 7/67* (2018.01); *A61K 8/0241* (2013.01); *A61K 8/19* (2013.01); *A61Q 19/00* (2013.01); *B82Y 30/00* (2013.01); *C01F 11/18* (2013.01); *C01F 11/185* (2013.01); *C08K 3/26* (2013.01); *C09C 1/02* (2013.01); *C09C 1/021* (2013.01); *C09C 3/04* (2013.01); *C09D 5/028* (2013.01); *C09D 7/61* (2018.01); *C09D 7/68* (2018.01); *C09D 175/06* (2013.01); *A61K 2800/10* (2013.01); *A61K 2800/412* (2013.01); *A61Q 3/02* (2013.01); *C01P 2004/03* (2013.01); *C01P 2004/51* (2013.01); *C01P 2004/62* (2013.01); *C01P 2004/64* (2013.01); *C01P 2006/12* (2013.01); *C01P 2006/22* (2013.01); *C01P 2006/60* (2013.01); *C08K 3/20* (2013.01); *C08K 2003/265* (2013.01); *Y10T 428/23943* (2015.04); *Y10T 428/23986* (2015.04); *Y10T 428/249953* (2015.04); *Y10T 428/249962* (2015.04); *Y10T 428/25* (2015.01); *Y10T 442/20* (2015.04)

(58) Field of Classification Search
CPC .......... C08K 3/26; C01F 11/18; C01F 11/185; C09C 1/021; C09C 3/04
USPC ....................................................... 524/425
See application file for complete search history.

(56) References Cited

U.S. PATENT DOCUMENTS

| | | | |
|---|---|---|---|
| 3,501,424 A | | 3/1970 | Imoto et al. |
| 3,604,634 A | * | 9/1971 | Windle .................. B02C 23/06 |
| | | | 241/16 |
| 3,664,912 A | | 5/1972 | Olson |
| 4,732,748 A | * | 3/1988 | Stewart ................. C01F 11/185 |
| | | | 162/181.2 |
| 5,171,631 A | * | 12/1992 | Adkins ................... C09C 1/021 |
| | | | 106/442 |
| 5,533,678 A | * | 7/1996 | Strauch ................. C01F 11/185 |
| | | | 241/16 |

(Continued)

FOREIGN PATENT DOCUMENTS

| | | | | |
|---|---|---|---|---|
| EP | 1764347 A1 | * | 3/2007 | ............ C01F 11/185 |
| GB | 208832 | | 1/1924 | |

(Continued)

OTHER PUBLICATIONS

Derwent Abstract (Acc. No. 1970-69712R, 1974, 2 pages).*

(Continued)

*Primary Examiner* — Brieann R Johnston
(74) *Attorney, Agent, or Firm* — Heslin Rothenberg Farley & Mesiti P.C.

(57) ABSTRACT

A coating composition comprising an aqueous dispersion of submicron natural ground calcium carbonate particles contained in a liquid binder, wherein the resultant coating may constitute either a clear coat or a glossing and opacifying coating, depending upon the presence of certain additives such as a mineral pigment (e.g., $TiO_2$). The composition is characterised in that comprises, in the case of a clear coating, at least one ground natural calcium carbonate having a median diameter of between 0.05 and 0.15 μm, while in the case of a glossing and opacifying coating, at least one ground natural calcium carbonate having a median diameter of between 0.05 and 0.3 μm and at least one pigment having a refractive index of greater than or equal to 2.5.

33 Claims, 2 Drawing Sheets

(56) References Cited

U.S. PATENT DOCUMENTS

| | | | |
|---|---|---|---|
| 6,572,694 B2* | 6/2003 | Towe | C09B 67/0033 106/464 |
| 6,777,466 B2 | 8/2004 | Eckstein et al. | |
| 6,897,281 B2 | 5/2005 | Lubnin et al. | |
| 2004/0161594 A1 | 8/2004 | Joyce et al. | |
| 2005/0004306 A1 | 1/2005 | Lubnin et al. | |
| 2006/0162884 A1 | 7/2006 | Gane et al. | |
| 2007/0141264 A1 | 6/2007 | Satgurunathan et al. | |
| 2007/0266898 A1 | 11/2007 | Gane et al. | |
| 2008/0182929 A1* | 7/2008 | Strepka | C09D 7/20 524/291 |
| 2009/0317626 A1 | 12/2009 | Tiarks et al. | |
| 2010/0048741 A1 | 2/2010 | Jang et al. | |
| 2010/0166967 A1* | 7/2010 | Fasano | C09D 5/028 427/385.5 |
| 2011/0046286 A1 | 2/2011 | Lubnin et al. | |
| 2011/0098376 A1* | 4/2011 | Sheerin | C08F 6/003 523/122 |
| 2013/0000518 A1* | 1/2013 | Raper | C09C 1/3684 106/448 |

FOREIGN PATENT DOCUMENTS

| | | |
|---|---|---|
| JP | 55016031 A | 2/1980 |
| JP | 61023658 A | 2/1986 |
| JP | 09194669 A | 7/1997 |
| JP | 2004315359 A | 11/2004 |
| JP | 200652352 A | 10/2006 |
| JP | 2006307002 A | 11/2006 |
| JP | 2007314919 A | 12/2007 |
| JP | 2009161708 A | 7/2009 |
| JP | 2009221409 A | 10/2009 |
| JP | 2009543916 A | 12/2009 |
| WO | 2004074574 A2 | 9/2004 |
| WO | 2004083316 | 9/2004 |
| WO | 2006008657 A3 | 1/2006 |
| WO | 2006079098 A1 | 7/2006 |
| WO | 2006123235 | 11/2006 |
| WO | 2007012935 A3 | 2/2007 |
| WO | 2007141271 A1 | 12/2007 |
| WO | 2008003672 A1 | 1/2008 |
| WO | 2008041715 A1 | 4/2008 |
| WO | 2009074651 A1 | 6/2009 |
| WO | 2011022582 A1 | 2/2011 |
| WO | 2011092152 A1 | 8/2011 |

OTHER PUBLICATIONS

Office Action dated Mar. 9, 2016 for Japanese Application No. 2013-554898.
International Search Report dated Dec. 4, 2012 for PCT Application No. PCT/EP2012/053089.
Written Opinion of International Searching Authority dated Dec. 4, 2012 for PCT Application No. PCT/EP2012/053089.
Chatfield "Painting Coatings" ed. Moscow, Chemistry 1968. pp. 372, 377, 380, 381-383.

* cited by examiner

COATING COMPOSITION COMPRISING SUBMICRON CALCIUM CARBONATE-COMPRISING PARTICLES, PROCESS TO PREPARE SAME AND USE OF SUBMICRON CALCIUM CARBONATE-COMPRISING PARTICLES IN COATING COMPOSITIONS

CROSS-REFERENCE TO RELATED APPLICATIONS

This is a divisional of U.S. application Ser. No. 13/980,386, filed Aug. 29, 2013, which is a U.S. National Phase of PCT Application No. PCT/EP2012/053089, filed Feb. 23, 2012, which claims priority to U.S. Provisional Application No. 61/446,006, filed Feb. 23, 2011, the contents of which are hereby incorporated herein by reference in their entirety.

TECHNICAL FIELD

The present invention relates to coating compositions comprising submicron natural ground calcium carbonate-comprising particles (hereafter SMGCC). The invention further relates to a process for preparing coating compositions containing SMGCC, and to the use of SMGCC in coating compositions. The coating composition(s), depending upon their composition, may be used to form either clear coatings, or else they may be formulated as glossing and opacifying coating compositions. The entire contents of provisional patent application No. 61/400,648 filed Jul. 30, 2010 and entitled "Coating Composition Comprising Submicron Calcium Carbonate Comprising Particles, Process to Prepare Same and Use of Submicron Calcium Carbonate-Containing Particles in Coating Compositions" are specifically incorporated herein by reference.

BACKGROUND AND DETAILED DESCRIPTION

The aqueous nanoparticle dispersion of this invention can be used to make coatings and films for porous and non-porous substrates, such as papers, non-woven materials, textiles, leather, wood, concrete, masonry, metals, house wrap and other building materials, fibreglass, polymeric articles, personal protective equipment (such as hazardous material protective apparel, including face masks, medical drapes and gowns and firemen's turnout gear) and the like. Applications include papers and non-woven materials, fibrous materials, films, sheets, composites and other articles, inks and decorative and industrial coatings, flock and other adhesives and personal care products such as skin care, hair care and nail care products, livestock and seed applications, and the like.

Any fibrous material can be coated, impregnated or otherwise treated with the compositions according to the invention by methods well known to those skilled in the art, including carpets as well as textiles used in clothing, upholstery, tents, awnings, airbags and the like. Suitable textiles include fabrics, yarns and blends, whether woven, non-woven or knitted and whether natural, synthetic or regenerated. Examples of suitable textiles include cellulose acetate, acrylics, wool, cotton, jute, linen, polyesters, polyamides, regenerated cellulose (i.e., rayon) and the like.

The compositions, depending upon their intended application, may be dispersed in a variety of binders including, but not limited to, vinyl-acrylic, styrene-acrylic, acrylic dispersions, solution acrylics, alkyds (e.g., SOYA, TOFA, sunflower, etc.), polyurethanes dispersed in either water or solvent, etc., hereinafter referred to as "binder media".

Additionally, the compositions according to the invention can be used as adhesives or to augment or supplement adhesive types well known to those skilled in the art. Thus, in the application discussed above wherein the compositions are used as adhesives or to augment or supplement various known adhesive types, particularly desirable properties can be obtained by varying the type and amount of the aqueous nanoparticles used, along with choosing a complementary binder medium from one or more of those listed above, or by incorporating other binder media that would be well known to those of ordinary skill in this art.

As noted above, coatings containing the compositions according to the invention may optionally be formulated as substantially transparent coatings, i.e., typically referred to as 'clear coats', or alternately as coatings that serve a glossing and opacifying function. The clear coating composites produced when the aqueous dispersions are applied and dried, exhibit excellent gloss and clarity. Moreover, so long as the $D_{98}$ particle size of the substantially dispersed nanoparticles contained in the coating composition is ≤350 nm, preferably ≤300 nm and the $D_{50}$ is ≤200 nm, preferably ≤150 nm, the coatings obtained will be essentially transparent, provided of course that they are free or essentially free of additional components which would comprise their transparency properties.

For purposes of exemplifying and not limiting, the invention, one useful binder medium for forming, e.g., clear coatings according to the invention are polymers containing ester groups such as, for example, polyesters, polyester-based polyurethanes, polyester-based polyureas and polyester-based polyamides. These various binders, however, have less than desirable water-resistance properties due to the hydrolysis group contained therein.

It has been determined, furthermore, that the water resistant properties of such polyester-based polyurethanes can be remarkably enhanced, without affecting the transparency properties of these materials to any significant degree, by combining with the polymer binder a substantially dispersed nano-particle proton scavenger, such as natural ground calcium carbonate-comprising particles. The resultant coating composition, therefore, which again is described only for exemplifying (and not limiting) the invention, thus constitutes a hydrolytically stable polyurethane nanocomposite comprising a solid polyester-polyurethane polymer binder containing proton-scavenger nanoparticles in a substantially dispersed form. One particular useful example of such a formulation would constitute a colloidally stable aqueous dispersion comprising water, a polyester-polyurethane polymer binder and substantially dispersed proton scavenger nanoparticles such as SMGCC.

In the meaning of the present invention the term "substantially dispersed" means that the nanoparticles are properly dispersed in the aqueous medium in order to prevent settling or syneresis of the nanoparticles. This is usually achieved via the addition of well-known dispersants comprising homo- or copolymer chains. If necessary, the chains may be partially or completely neutralized by cations such as sodium, lithium, magnesium, calcium, potassium or ammonium.

Coatings having the composition of the exemplary formulation described above, therefore, constitute polyurethane compositions which, e.g., have improved hydrolytic stability over prior art polyurethane compositions. As used herein the term polyurethane is used generically to describe polymers including oligomers (e.g., prepolymers) which contain the urethane group, i.e., —O—C(=O)—NH— regardless of how they are made. As is well known, these polyurethanes can contain additional groups such as urea, allophanate, biuret, carbodiimide, oxazolidinyl, isocynurate, uretdione, alcohol, amine, hydrazide, siloxane, silane, ketone, olefin, etc., in addition to the urethane groups.

This invention includes, as noted herein the use of substantially dispersed nanoparticles (referring to the primary crystallites or particles of the proton scavenger and or the aggregates of the proton scavenger) of proton scavenger nanoparticles to enhance the water-resistant (hydrolytic stability) of thermoplastic polyurethanes containing polyester segments within the polyurethane polymer or prepolymer. Thermoplastic polyurethanes are made with the same components as waterborne polyester polyurethanes (polyurethane dispersions in water) immediately below but typically the thermoplastic polyurethanes have substantially less or no water-dispersibility enhancing compound(s). In one embodiment the hydrolytically stable polyurethane is a thermoplastic polyurethane. The technology for making and using thermoplastic polyurethanes are well known and described for example in U.S. Pat. No. 6,777,466 B2 and J. K. Backus et al., "Polyurethanes," in: Encyclopedia of Polymer Science and Engineering. Vol. 13, H F. Mark et al., Ed, pp. 243-303 (1988), the entire disclosure of which is incorporated herein by reference.

Furthermore, the invention in one embodiment relates to polyester polyurethanes which are derived from aqueous dispersions and which, when dried and cured, produce solid polyester segment containing polyurethane products which are tough and, depending on the other ingredients present (e.g., absence of $TiO_2$ or other pigment), can be a transparent.

Further in accordance with this invention, it has been found that the susceptibility of polyester polyurethanes to degrade through hydrolysis can be essentially completely eliminated by incorporating into the polymer a substantially dispersed nanoparticle (referring to the aggregate and/or the ultimate particles/crystallite) proton scavenger.

Certain materials are known to react with, bind to, or otherwise capture protons, i.e., hydrogen ions, when exposed thereto in solid, liquid and/or gaseous media. Calcium carbonate, is a good example as are the other alkali and earth-alkali metal carbonates, i.e., $Li_2CO_3$, $BeCO_3$, $MgCO_3$, $SrCO_3$, $BaCO_3$, and $RaCO_3$. Other examples of carbonates which will scavenge protons include carbonates of Fe(II), Fe(III), Mn(II), Zn, Ag, Hg(I), Hg(II), Cu(II), Pb(II), Bi(III).

Calcium carbonate has the formula $CaCO_3$. It is a common substance found in rock in all parts of the world, and is the main component of shells of marine organisms, snails, pearls, and eggshells. Calcium carbonate is found naturally as the following minerals and rocks: aragonite, calcite, vaterite or (μ-CaCO3), chalk, limestone, marble, travertine. The vast majority of calcium carbonate used in industry is extracted by mining or quarrying. Pure calcium carbonate (e.g., for food or pharmaceutical use), can be produced from a pure quarried source (usually marble). Ground calcium carbonate (GCC) is produced through mechanical grinding of naturally occurring calcium carbonate rocks: marble, limestone and chalk. GCC in pigment formulations provides good rheology and high brightness at low cost. Alternatively, crude calcium carbonate is calcinated into calcium oxide (quicklime). Water is added to give calcium hydroxide, and carbon dioxide is passed through this solution to precipitate the desired calcium carbonate, known as precipitated calcium carbonate (PCC). This process produces very pure calcium carbonate crystals. The crystals can be tailored to a variety of different shapes and sizes, depending on the specific reaction process used. The three main shapes of PCC crystals are aragonite, rhombohedral, and scalenohedral. Within each crystal type, the PCC process can control mean particle size, size distribution, and surface area. Precipitated calcium carbonate is used as a mineral pigment throughout the world for paper production. It is valued for its high brightness and light scattering characteristics in paper filling and coating applications.

Other examples of inorganic compounds which will scavenge protons include silicates of Ba, Ca, Mg, Al, Cr(III), Fe(II), Fe(III), Mn(II), Zn, Ag, Cu(II), Pb(II); sulfides of Fe(II), Mn(II), Zn, Ag, Hg(I), Hg(II), Cu(II), Pb(II), Bi(III), Sn(II); oxides and hydroxides of the above metals; and hydroxyapatite, which is a naturally occurring mineral form of calcium apatite.

Examples of organic compounds which will scavenge protons include 1,8-bis-(dimethylamino)naphthalene, 1,8-bis(hexamethyltriaminophosphazenyl)naphthalene and 2,6-di-tert-butylpyridine.

Any combination of the above scavenges may be used.

In accordance with this invention, it has been found that these proton scavengers materials form will substantially reduce or even completely eliminate the susceptibility of polyester polyurethanes to degrade though hydrolysis without introducing any significant haze into the polymer, but only if they are incorporated into the polymer in a substantially dispersed nanoparticle and/or high surface area form.

In this regard, nanoparticles are typically obtained commercially in powder or dispersion form, both aqueous and organic. Although the individual/primary (crystallites for $CaCO_3$) particles in these products may be in the nano size range, these particles usually combine into larger agglomerates in which the nanoparticles are relatively closely-packed with one another usually in three dimensions. Therefore, when these nanoparticle powders and dispersions are used to make nanoparticle-containing polymers, the nanoparticles remain in the form of these larger agglomerates. In other words, the nanoparticles are not substantially dispersed in the polymer mass. In accordance with this invention, it has been found that proton scavenger nanoparticles will substantially reduce or even completely eliminate the susceptibility of polyester polyurethanes to degrade though hydrolysis, but only if they are incorporated into the polymer mass ultimately formed in a substantially dispersed and/or high surface area form.

Figure 1A:
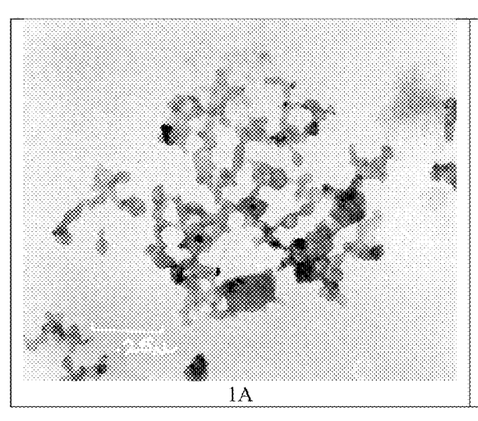
FIGS. 1A and 1B are photomicrographs of Omya XC-6600-34 $CaCO_3$.
Figure 1B:
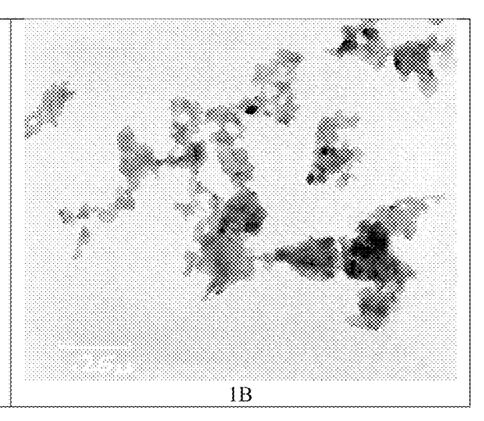

An example of substantially dispersed (but loosely aggregated having a high surface area (e.g. 41 $m^2/g$) arrangement is shown in FIGS. 1A and 1B. The primary nano crystallites of Omya XC-6600-34 from Omya form flocks of various shape and dimensions with a substantial portion of the surface exposed to the matrix they are in. From this perspective, the most effective form of flocculation is a trains or chains of particles. Such an arrangement into relatively large floc particles can introduce some haze to the nanocomposites, but will still be effective in retarding ester hydrolysis because large portion of the nanoparticles surfaces is exposed to the matrix.

In one embodiment where the ultimate particle/crystallite diameter is small, desirably the $D_{50}$ is less than 1 micron, more desirably less than 500 nm, more desirably less than 100 nm, and preferably less than 50 nm. In a similar embodiment, desirably the $D_{90}$ is less than 1 micron, more desirably less than 500 nm, more desirably less than 100 nm, and preferably less than 50 nm. In one embodiment, the nitrogen BET surface area is greater than 20 $m^2/g$; more desirably greater than 30 $m^2/g$; still more desirably greater than 35 $m^2/g$ and preferably about 40 or more $m^2/g$.

In one embodiment, the particle size of the proton scavenger nanoparticles when in the substantially dispersed form desired by this invention can vary widely, and essentially any particle size in the nanoparticle size range can be used. For the purposes of the present invention, nano particles and substantially dispersed nanoparticles are defined as particles which have at least one of the three dimensions of less than about 250 nm ($D_{90}$) but will normally be less than about 150 nm. In other embodiments, the mean particle size will be about 100 nm or less ($D_{90}$), 75 nm or less, or even 50 nm or less. In some embodiments, the particle size may even be as low as 25 nm or less, 10 nm or less, or even 5 nm or less. In general, the mean particle size, $D_{50}$, of these substantially dispersed nanoparticles may be as large as 250 nm (nanometers) but will normally be less than 100 nm. Substantially dispersed nanoparticles having a mean particle size of about 75 nm or less, more typically 50 nm or less, or even 40 nm or less are interesting. In other embodiments, the mean particle size will be 30 nm or less, 25 nm or less, or even 10 nm or less. In some embodiments, the particle size may even be as low as 5 nm or less, 2 nm or less, or even 1 nm or less.

Particle size is usually characterized by particle size distribution, since all particles in a batch of particles do not have an identical particle size. Thus, in some embodiments of the invention, it is desirable that the nanoparticle batch have a $D_{90}$ of less than 250 nm (i.e., 90% of volume of the particles in the batch have equivalent diameters less than 250 nm). Nanoparticle batches with $D_{90}$'s of 150 nm or less, 100 nm or less, more typically 75 nm or less, or even 50 nm or less, 25 nm or less, 10 nm or less, or even 5 nm or less are especially interesting.

Of particular interest are nanoparticle batches having $D_{90}$'s of about 100 nm or less, and especially 75 nm or less, or even 50 nm or less, since nanoparticles of this size when substantially dispersed in a polymer matrix become essentially transparent to the naked eye.

The aqueous nanoparticle/polyester-polyurethane dispersions of this invention, both in prepolymer and chain extended form, can be used to make coatings and films for porous and non-porous substrates such as papers, non-woven materials, textiles, leather, wood, concrete, masonry, metals, house wrap and other building materials, fiberglass, polymeric articles, personal protective equipment (such as hazardous material protective apparel, including face masks, medical drapes and gowns, and firemen's turnout gear), and the like. Applications include papers and non-wovens, fibrous materials, films, sheets, composites, and other articles, inks and printing binders, flock and other adhesives, and personal care products such as skin care, hair care, and nail care products, livestock and seed applications, and the like.

Any fibrous material can be coated, impregnated or otherwise treated with the compositions of this invention by methods well known to those skilled in the art, including carpets as well as textiles used in clothing, upholstery, tents, awnings, air bags, and the like. Suitable textiles include fabrics, yarns, and blends, whether woven, non-woven, or knitted, and whether natural, synthetic, or regenerated. Examples of suitable textiles include cellulose acetate, acrylics, wool, cotton, jute, linen, polyesters, polyamides, regenerated cellulose (Rayon), and the like.

Compositions of this invention can also be used to produce articles made of stand-alone films and objects such as personal protective equipment. Examples of protective items include gloves and condoms.

In addition, the compositions of this invention can be used as adhesives or to augment or supplement adhesive types well known to those skilled in the art. For example, particular adhesive properties can be achieved by varying type and amount of isocyanates, type, amount, and molecular weight of polyols, and the amount of poly(alkylene oxide) side chain units.

The polyester-polyurethane nanoparticle composites produced when the aqueous dispersions of this invention are applied and dried, whether or not the polyester-polyurethane is chain extended, exhibit exceptional resistance to degradation by hydrolysis, in particular a resistance to hydrolysis comparable to that of the much more expensive polycarbonate polyurethane resins. Moreover, so long as the $D_{90}$ particle size of the substantially dispersed nanoparticles used is ≤75 nm, preferably ≤50 nm or even ≤40 nm, the polyurethanes obtained will be essentially transparent, provided of course that they are free or essentially free of other materials which would compromise their transparency properties.

Finally, the principles of the present invention can be applied to other technologies for manufacturing aqueous polyurethane dispersions. For example, this invention can be applied to the technique for manufacturing breathable polyurethane dispersions (i.e. dispersions which form layers of breathable polyurethanes) described in U.S. Pat. No. 6,897,281, as well as to the technique for manufacturing core-shell polyurethane dispersions described in U.S. Published Patent Application No. 20050004306. The disclosures of the above patent and published applications are incorporated herein by reference.

Polyurethanes based on polyester macroglycols are known to be susceptible to hydrolysis. The hydrolytic stability of the improved product is attributed to the presence of a proton scavenger in highly dispersed form having significant surface area (increasing the probability that the proton scavenger will be able to scavenge protonic species before the cause hydrolytic chain scission in the polyester portion of the polyurethane). The polyurethane can be in the form of a film, coating or shaped article. The proton scavenger is preferably an inorganic carbonate salt such as calcium carbonate. If the aggregates of the proton scavenger are small relative to the wavelength of light the polyurethane composition will be substantially transparent to visible light. If the proton scavenger, e.g. calcium carbonate, is comprised of loosely aggregated primary crystallites, that are in the 5-100 nanometer weight average diameter, it will have high surface area (e.g. >40 $m^2/g$) will be effective at scavenging protons.

In order to further exemplify the clear coatings formulated according to the invention, several working examples of such clear coat formulations are provided below. In these examples, the following raw materials were used:

DOW—SG30 Acrylic Latex (binder medium)
Bayhydrol 110—Polyurethane Dispersion (binder medium)
Deionized Water
Various Omya experimental SM-GCC slurries.

In addition, the following analytical and testing procedures were used in carrying out these examples:
Gloss was measured at 20°, 60°, and 75° angles utilizing a Micro TriGloss unit from BYK-Gardner, catalog #4446
Sheen at 85° angle utilizing a Micro TriGloss unit from BYK-Gardner, catalog #4446

Solids Content—total solids were measured by Moisture/Solids Analyzer

Toledo HB 43 (Mettler Toledo Corporation)

pH Measurements—pH readings were taken using pH 510 Meter, a pH meter from BYK-Gardner, Catalog # PH-2643.

Gloss/Haze. The preferred evaluation of haze is visual because perceived haze and clarity are one of the most important properties of coatings and other articles. Haze can also be measured by objective instrumental means. Examples include the method described in ASTM D 1003-07 "Standard Test Method for Haze and Luminous Transmittance of Transparent Plastics", measurement of gloss at different angles, measurement of L,a,b values, and also other methods described in ASTM Guide E179-96(2003) "Standard Guide for Selection of Geometric Conditions for Measurement of Reflection and Transmission Properties of Materials", D1455 "Test Method for 60-deg Specular Gloss of Emulsion Floor Polish", D1746 "Test Method for Transparency of Plastic Sheeting", D4039 "Test Method for Reflection Haze of High-Gloss Surfaces", D4061 "Test Method for Retroreflectance of Horizontal Coatings" and D523 "Test Method for Specular Gloss".

Preparation of a Clear Gloss Coating Containing Calcium Carbonate Nanoparticle Dispersion In each case an aqueous dispersion of substantially dispersed calcium carbonate nanoparticles was produced by from the following ingredients:

Ingredients Used in Example 1

| Ingredient | Wt., g |
|---|---|
| Omya experimental SMGCC (Calcium Carbonate) | 59.7 |
| Water | 12.3 |
| DOW - SG30 Acrylic Latex binder | 100 |
| TOTAL | 172 |

Ingredients Used in Example 2

| Ingredient | Wt., g |
|---|---|
| Omya experimental SMGCC (Calcium Carbonate) | 61.2 |
| Water | 10.8 |
| DOW - SG30 Acrylic Latex binder | 100 |
| TOTAL | 172 |

Ingredients Used in Example 3

| Ingredient | Wt., g |
|---|---|
| Omya experimental SMGCC (Calcium Carbonate) | 62.2 |
| Water | 9.8 |
| DOW - SG30 Acrylic Latex binder | 100 |
| TOTAL | 172 |

Ingredients Used in Example 4

| Ingredient | Wt., g |
|---|---|
| Omya experimental SMGCC (Calcium Carbonate) | 61.7 |
| Water | 10.3 |
| DOW - SG30 Acrylic Latex binder | 100 |
| TOTAL | 172 |

Ingredients Used in Example 5

| Ingredient | Wt., g |
|---|---|
| Omya experimental SMGCC (Calcium Carbonate) | 61.2 |
| Water | 10.8 |
| DOW - SG30 Acrylic Latex binder | 100 |
| TOTAL | 172 |

Ingredients Used in Example 6

| Ingredient | Wt., g |
|---|---|
| Omya experimental SMGCC (Calcium Carbonate) | 62.1 |
| Water | 9.9 |
| DOW - SG30 Acrylic Latex binder | 100 |
| TOTAL | 172 |

Ingredients Used in Example 7

| Ingredient | Wt., g |
|---|---|
| Omya experimental SMGCC (Calcium Carbonate) | 60.2 |
| Water | 11.8 |
| DOW - SG30 Acrylic Latex binder | 100 |
| TOTAL | 172 |

Ingredients Used in Example 8

| Ingredient | Wt., g |
|---|---|
| Omya experimental SMGCC (Calcium Carbonate) | 61.3 |
| Water | 10.7 |
| DOW - SG30 Acrylic Latex binder | 100 |
| TOTAL | 172 |

Ingredients Used in Example 9

| Ingredient | Wt., g |
|---|---|
| Omya experimental SMGCC (Calcium Carbonate) | 60 |
| Water | 12 |
| DOW-SG30 Acrylic Latex binder | 100 |
| TOTAL | 172 |

Ingredients Used in Example 10

| Ingredient | Wt., g |
|---|---|
| Omya experimental SMGCC (Calcium Carbonate) | 60.6 |
| Water | 11.4 |
| DOW-SG30 Acrylic Latex binder | 100 |
| TOTAL | 172 |

TABLE 1

| | GLOSS MEASUREMENT | | | | Malvern D(50) | Malvern D(98) |
|---|---|---|---|---|---|---|
| | 75° | 20° | 60° | 85° | | |
| SG 30 Control | 93 | 63.3 | 83.3 | 92.5 | N/A | N/A |
| Example 1 | 88.4 | 33 | 70.7 | 89.9 | 0.12 | 0.3 |
| Example 2 | 83.7 | 19 | 60.2 | 91 | 0.12 | 0.4 |
| Example 3 | 85.1 | 22.6 | 61.5 | 87.2 | 0.13 | 0.5 |
| Example 4 | 83.2 | 17.7 | 57.8 | 90.5 | 0.13 | 0.3 |
| Example 5 | 88.1 | 33.1 | 69.6 | 89 | 0.12 | 0.4 |
| Example 6 | 83.6 | 16.6 | 56.5 | 91.4 | 0.13 | 0.5 |
| Example 7 | 80.3 | 14.5 | 53 | 88.7 | 0.12 | 0.3 |
| Example 8 | 88.4 | 36.6 | 71.9 | 89.8 | 0.13 | 0.4 |
| Example 9 | 82.2 | 16.8 | 54.2 | 88.5 | 0.13 | 0.5 |
| Example 10 | 81.5 | 16.2 | 53.9 | 90.2 | 0.13 | 0.6 |

The samples made with Dow SG-30 all acrylic latex were prepared using a Premier Mill Model # CM 100 high speed dissolver with a 2.5 in blade. They were dispersed for 30 minutes at 900 rpm.

Ingredients Used in Example 11

| Ingredient | Wt., g |
|---|---|
| Omya experimental SMGCC (Calcium Carbonate) | 2.3 |
| Bayhydrol 110 PUD binder | 75 |
| TOTAL | 77.3 |

Ingredients Used in Example 12

| Ingredient | Wt., g |
|---|---|
| Omya experimental SMGCC (Calcium Carbonate) | 2.4 |
| Bayhydrol 110 PUD binder | 75 |
| TOTAL | 77.4 |

Ingredients Used in Example 13

| Ingredient | Wt., g |
|---|---|
| Omya experimental SMGCC (Calcium Carbonate) | 2.4 |
| Bayhydrol 110 PUD binder | 75 |
| TOTAL | 77.4 |

Ingredients Used in Example 14

| Ingredient | Wt., g |
|---|---|
| Omya experimental SMGCC (Calcium Carbonate) | 2.8 |
| Bayhydrol 110 PUD binder | 75 |
| TOTAL | 77.8 |

Ingredients Used in Example 15

| Ingredient | Wt., g |
|---|---|
| Omya experimental SMGCC (Calcium Carbonate) | 2.8 |
| Bayhydrol 110 PUD binder | 75 |
| TOTAL | 77.8 |

Ingredients Used in Example 16

| Ingredient | Wt., g |
|---|---|
| Omya experimental SMGCC (Calcium Carbonate) | 4.6 |
| Bayhydrol 110 PUD binder | 75 |
| TOTAL | 79.6 |

Ingredients Used in Example 17

| Ingredient | Wt., g |
|---|---|
| Omya experimental SMGCC (Calcium Carbonate) | 4.8 |
| Bayhydrol 110 PUD binder | 75 |
| TOTAL | 79.8 |

Ingredients Used in Example 18

| Ingredient | Wt., g |
|---|---|
| Omya experimental SMGCC (Calcium Carbonate) | 4.8 |
| Bayhydrol 110 PUD binder | 75 |
| TOTAL | 79.8 |

Ingredients Used in Example 19

| Ingredient | Wt., g |
| --- | --- |
| Omya experimental SMGCC (Calcium Carbonate) | 5.6 |
| Bayhydrol 110 PUD binder | 75 |
| TOTAL | 80.6 |

Ingredients Used in Example 20

| Ingredient | Wt., g |
| --- | --- |
| Omya experimental SMGCC (Calcium Carbonate) | 5.6 |
| Bayhydrol 110 PUD binder | 75 |
| TOTAL | 80.6 |

TABLE 2

Bayhydrol with 5% GCC loading

| | GLOSS MEASUREMENT | | |
| --- | --- | --- | --- |
| Bayhydrol 110 | 20° | 60° | 85° |
| (Control) | 67.5 | 90.9 | 95.9 |
| Example 11 | 65.8 | 87.2 | 96.1 |
| Example 12 | 74.1 | 88.6 | 97.9 |
| Example 13 | 71.3 | 88.4 | 97.7 |
| Example 14 | 72.5 | 88.5 | 98 |
| Example 15 | 75.6 | 88.4 | 97.8 |

TABLE 3

Bayhydrol with 10% GCC loading

| | GLOSS MEASUREMENT | | |
| --- | --- | --- | --- |
| Bayhydrol 110 | 20° | 60° | 85° |
| (Control) | 67.5 | 90.9 | 95.9 |
| Example 16 | 60 | 87 | 95 |
| Example 17 | 64.2 | 89.9 | 95.5 |
| Example 18 | 64.9 | 86.6 | 95.5 |
| Example 19 | 64.3 | 87 | 95.8 |
| Example 20 | 62.1 | 86.3 | 95.7 |

The samples made with Bayhydrol 110 were prepared using a Speed Mixer Model # DAC 150.1 FVZ-K. They were dispersed for 1 min at 2500 rpm.

Turning next, then, to a discussion of an alternate embodiment of the present invention wherein the aqueous nanoparticle dispersions described herein are utilized in forming glossing and opacifying coating compositions, it is noted that mineral pigments are widely used in known glossing and opacifying coating systems, not only to decrease formulation costs but further to improve certain properties of the coating formulation during its preparation or storage, or during or following its application to a substrate. In the realm of paint formulations, coating systems almost invariably implement titanium dioxide.

In the context of paint applications, titanium dioxide ($TiO_2$) is commonly used, particularly in its rutile form, for providing significant opacity or hiding power. Titanium dioxide pigments marketed for use in paint formulation are well known to present a narrow particle size distribution along with a median particle diameter of between 0.2 and 0.6 µm, depending on the material and the mean particle size measurement method. Zinc sulphide and zinc oxide are similarly employed.

Titanium dioxide suffers however from being relatively high in cost, resulting in a continuing desire to find lower-cost $TiO_2$ partial replacement pigments that do not translate in a reduction of optical and other coating composition properties.

GB1404564 describes ultrafine natural calcium carbonate filled paints and pigments, wherein said natural calcium carbonate has a particle diameter of from 0.5 to 4 µm and is employed to partially replace titanium dioxide. In this vein, Imerys has commercialised Polcarb, said to be suitable for glossing paint formulations, which has a mean particle size of 0.9 µm. However, such natural calcium carbonate products do not allow the replacement of a part of $TiO_2$ in glossing paint formulation having a pigment volume concentration below the critical pigment volume concentration without loss of gloss or opacity.

For the purpose of describing the glossing and opacifying coating compositions according to the present invention, the pigment volume concentration (PVC) is understood to refer to the fraction, quoted in %, of pigment volume relative to the total volume of the pigment plus the other components of the formulation, i.e., it accounts for the pigment volume relative to the total formulation volume.

The critical pigment volume concentration (CPVC) is defined as the pigment volume concentration whereupon the resin component of the coating formulation is no longer sufficient to entirely coat all of the pigment particles in a coating. It is well known that above the CPVC, formulations generally provide a matt finish. By contrast glossy paint formulations implement a PVC that is below the CPVC.

Figure 2:
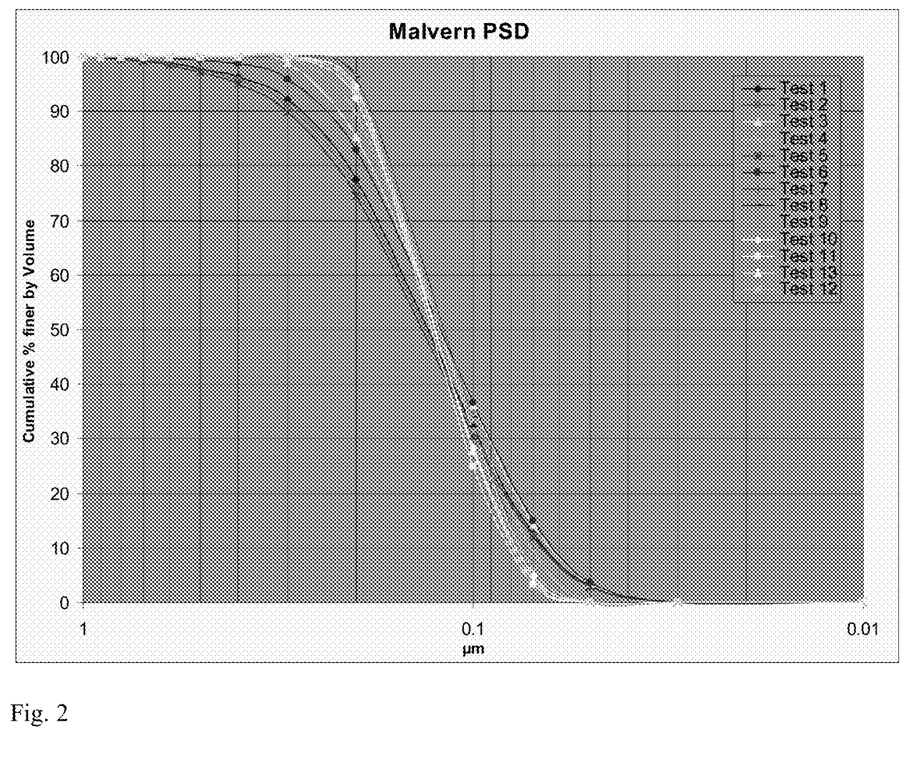
FIG. 2 is a series of particle size distribution curves containing data for a series of samples whose $D_{98}$ value is <0.3 μm. The values for $D_{90}$, $D_{50}$ and $D_{20}$ for these samples can be determined by comparing the x and y-axis.

U.S. Pat. No. 5,171,631 discloses a coating composition for developing hiding on a suitable substrate, the coating composition having a pigment volume concentration (PVC) up to a critical pigment volume concentration (CPVC) and a pigment system comprising about 70-98% by volume of titanium dioxide and about 2-30% by volume of an aluminium trihydrate (ATH) spacer/extender pigment having a medium particle size of about 0.2 microns. FIG. 1 of U.S. Pat. No. 5,171,631 shows a $D_{98}/D_{50}$ ratio value of approximately 2.7, which corresponds to a relatively narrow particle size distribution. Although it is stated that, provided this ATH has a median particle size and particle size distribution generally similar to the median particle size and particle size distribution curve of $TiO_2$, a portion of $TiO_2$ may be replaced with an equal volume of ATH with no loss of hiding, FIG. 2 of U.S. Pat. No. 5,171,631 shows that the ATH-$TiO_2$-comprising paint formulations generally fail to achieve the same opacity values as the control paint formulation comprising $TiO_2$ alone.

Natural ground calcium carbonate as opposed to its synthetic counterpart, precipitated calcium carbonate (PCC), generally suffers from a broad particle size distribution and irregular particle shapes. Indeed, as natural ground calcium carbonate is prepared by the grinding down of mined calcite, marble, chalk or limestone-containing stones, it is difficult to ensure that these stones are ultimately fractioned to form fine particles having a very uniform particle size.

By contrast, PCC is formed by a process of building crystals around nucleation sites. Control of nucleation and particle size development, particularly in the size domain under a few micrometers, during PCC precipitation has, over the years, become a well studied science and PCC particles having small and very uniform particle sizes and shapes are now widely available. As in U.S. Pat. No. 5,171,631, the advantages of employing a uniform particle size product as a titanium dioxide spacer are alluded to in the publication made at http://www.specialtyminerals.com/specialty-applications/specialty-markets-for-minerals/paint-and-coatings/precipitated-calcium-carbonate-pcc-in-paint/: "precipitated calcium carbonate (PCC) is most commonly used in paint as an extender for titanium dioxide, or $TiO_2$. The small and narrowly distributed PCC particles help space the individual $TiO_2$ particles and maximize their hiding power." In this domain, Specialty Minerals advertises Albafil PCC, a fine, 0.7 micron prismatic calcite, and a range of ultrafine or nano PCCs, namely Calofort S PCC, Calofort U PCC, Ultra-Pflex PCC and Multifex MM PCC, each having a median diameter of 0.07 micron.

In view of the above-discussed teachings found in the prior art, it was remarkable that the present inventors found that a ground natural calcium carbonate that is finer than ground natural calcium carbonate products previously offered in this domain, may be used to form an aqueous nanoparticle dispersion in one or more of the binder systems described above for use in forming a variety of (1) clear-coat coating compositions (see the discussion above), as well as serving as (2) a $TiO_2$ replacement or complementary pigment in the formation of glossing and opacifying coating compositions, even in the case when this ground natural calcium carbonate features a relatively broad particle size distribution and/or a median diameter that is different from that of $TiO_2$. By contrast to the results of U.S. Pat. No. 5,171,631 achieved with ATH, the ground natural calcium carbonate employed in the present invention not only more fully maintains the gloss and opacity of the paint formulation when used to replace part of the formulation $TiO_2$ at constant PVC, it may even lead to a gloss and/or opacity improvement.

One embodiment of a glossing and opacifying coating composition according to the invention is a composition having a PVC of from 5% up to the CPVC and characterised in that comprises at least one ground natural calcium carbonate having a median diameter (d50 (Mal)) of between 0.05 and 0.3 μm, (hereafter submicron ground natural calcium carbonate, SMGCC), and at least one pigment having a refractive index of greater than or equal to 2.5.

For the purpose of describing the glossing and opacifying coating compositions of the present application, CPVC was determined according to the measurement method given in the examples section below.

Moreover, for the purpose of further describing the glossing and opacifying coating compositions according to the present invention, the median diameter (d50 (Mal)) and d98 (Mal) were measured according to the measurement method provided in the examples section below.

Another object of the present invention resides in a process to prepare a glossing and opacifying coating composition having a PVC of from 5% up to the CPVC, characterised in that:
a) at least one ground natural calcium carbonate (SMGCC) having a $D_{50}$ (Mal) of between 0.05 and 0.3 μm is provided;
b) at least one pigment having a refractive index of greater than or equal to 2.5 is provided;
c) at least one resin (binder) is provided;
d) the SMGCC of step a) is mixed with the pigment of step b) and the resin of step c).

A third object of producing the glossing and opacifying coatings according to the present invention lies in the use of at least one ground natural calcium carbonate having a d50 (Mal) of between 0.05 and 0.3 μm, in a coating composition comprising at least one pigment having a refractive index of greater than or equal to 2.5, characterised in that for a coating composition having a constant PVC in the range of from 5% up to the CPVC, the gloss and/or opacity of the composition is equal to or greater than the gloss and/or opacity of the same composition implementing the pigment having a refractive index of greater than or equal to 2.5 in place of the ground natural calcium carbonate having a d50 of between 0.05 and 0.3 μm.

The gloss of a coating composition applied to a substrate was measured according to the measurement method provided in the examples section below.

The opacity of a coating composition applied to a substrate was measured according to the measurement method provided in the examples section below.

In order to more thoroughly describe the formulation of glossing and opacifying coating compositions according to the invention, the following examples are provided below.

A first embodiment of such a glossing and opacifying coating comprises a coating composition having a PVC of from 5% up to the CPVC and characterised in that comprises at least one ground natural calcium carbonate having a median diameter ($D_{50}$ (Mal)) of between 0.05 and 0.3 μm (hereafter submicron ground natural calcium carbonate, SMGCC), and at least one pigment having a refractive index of greater than or equal to 2.5. Preferably, the coating composition has a PVC of from 15 to 25%.

Preferably, the SMGCC has a median diameter ($D_{50}$ (Mal)) of between 0.1 and 0.3 μm.

In another embodiment, the SMGCC has a $D_{98}/D_{50}$ (Mal) of greater than 3. As indicated above and in contrast to the prior art, this ground natural calcium carbonate may, in an optional embodiment, have a particle size distribution that is broad and dissimilar to the particle size distribution said pigment having a refractive index of greater than or equal to 2.5 employed in the composition. Indeed, even a bi- or multimodal SMGCC particle size distribution may be envisioned.

In a preferred embodiment, said SMGCC has a $D_{98}$ of less than or equal to 1 μm, more preferably of less than or equal to 0.8 μm, even more preferably of less than or equal to 0.6 μm, and even more preferably of less than or equal to 0.4 μm.

Preferably, the SMGCC has a refraction index of approximately 1.5 to 1.7.

In another preferred embodiment, the pigment having a refractive index of greater than or equal to 2.5 is selected from one or more of the following: titanium dioxide and/or zinc sulphide and/or zinc oxide. In a more preferred embodiment, the pigment having a refractive index of greater than or equal to 2.5 is titanium dioxide. In such a case, it is preferred that the titanium dioxide:SMGCC weight ratio is of 70:30 to 98:2, and it is even more preferred that the titanium dioxide:SMGCC weight ratio is of 85:15 to 90:10.

In an alternate embodiment, the pigment contributing to the PVC of the composition is a mixture of at least one pigment having a refractive index of greater than or equal to 2.5, SMGCC and one or more of the following: clay, talc, magnesium carbonate, PCC, barium sulphate, mica and bentonite. In the case where magnesium carbonate is implemented in combination with SMGCC, this may be in the form of a dolomite.

This coating composition is characterised in that when all of said SMGCC is replaced by said pigment having a refractive index of greater than or equal to 2.5 while maintaining a constant PVC value in the range of from 15% up to the CPVC, the gloss of the SMGCC-comprising composition is within 10% of the gloss of the composition wherein the SMGCC is fully replaced by said pigment having a refractive index of greater than or equal to 2.5. Preferably, the gloss of the SMGCC-comprising composition is within 5%, and more preferably within 3%, of the gloss of the composition having only said pigment having a refractive index of greater than or equal to 2.5.

As shown in the examples below, it is not necessary that the SMGCC have a median diameter ($D_{50}$ (Mal)) that is equivalent to the median diameter ($D_{50}$ (Mal)) of said pigment having a refractive index of greater than or equal to 2.5, though this embodiment is not excluded from the present invention. The median diameter ($D_{50}$ (Mal)) of SMGCC may differ from the median diameter ($D_{50}$ (Mal)) of said pigment having a refractive index of greater than or equal to 2.5 by up to approximately 0.4 μm.

As also demonstrated by the examples below, said SMGCC may feature a broad and even non-uniform particle size distribution relative to the distribution of the pigment having a refractive index of greater than or equal to 2.5 is, though again this does not exclude the case where the particle size distributions of SMGCC and the pigment having a refractive index of greater than or equal to 2.5 is are similar in breadth.

Alternatively, the gloss of the SMGCC-comprising composition may be increased by at least 1% relative to the gloss of the composition wherein the SMGCC is fully replaced by the pigment having a refractive index of greater than or equal to 2.5. Relative to this embodiment, the gloss of the SMGCC-comprising composition is preferably increased by at least 5% relative to the gloss of the composition wherein the SMGCC is fully replaced by the pigment having a refractive index of greater than or equal to 2.5.

In a preferred embodiment, said SMGCC is dispersed with one or more dispersants. Conventional dispersants known to the skilled person can be used. The dispersant can be anionic, cationic or non-ionic. A preferred dispersant is polyacrylic acid.

The coating compositions according to the present invention (i.e., when used in forming the clear coatings as well as glossing and opacifying coatings) may be applied to a variety of substrates as discussed above, including but not limited to, concrete, wood, paper, metal and board.

In a preferred embodiment, the coating composition is applied to a substrate in an amount so as to form a layer having a thickness of between 100 and 400 um.

Following application to a substrate, a glossing and opacifying coating composition according to the invention preferably provides a gloss measured at 60° of greater than 70%. Furthermore, following application to a substrate, the coating composition preferably provides an opacity (contrast ratio) of greater than 97%.

The present coating compositions may further include one or more of the following: optical brightener, resin (such as a latex or acrylate-based binder, preferably in the form of an aqueous emulsion), defoamer, thickener, solvent, glycol ethers and dispersant. Preferably, the coating composition has a Brookfield viscosity of from 200 to 500 mPa·s, as measured according to the measurement method provided in the examples below.

Process For Preparing a Glossing/Opacifying Coating Composition in Accordance With the Present Invention The process results in the preparation of a coating composition having a PVC of from 5% up to the CPVC, characterised in that:
a) at least one ground natural calcium carbonate (SMGCC) having a $D_{50}$ of between 0.05 and 0.3 μm is provided;
b) at least one resin (binder) is provided;
c) the SMGCC of step a) is mixed with the resin of step b).

The SMGCC of step a) may be provided in the form of an aqueous suspension, an aqueous dispersion or as a dry powder. In a preferred embodiment, the SMGCC of step a) is provided in the form of an aqueous suspension or dispersion.

The resin is preferably a latex and/or acrylate-based binder, said acrylate-based binder preferably being in the form of an aqueous emulsion.

Use of SMGCC in Glossing/Opacifying Coating Compositions

Another object of the present invention lies in the use of at least one ground natural calcium carbonate having a $D_{50}$ (Mal) of between 0.05 and 0.3 μm, in a glossing/opacifying coating composition, characterised in that for a coating composition having a constant PVC in the range of from 15% up to the CPVC, the gloss and/or opacity of the composition is equal to or greater than the gloss and/or opacity of the same composition implementing $TiO_2$ in place of said ground natural calcium carbonate having a d50 of between 0.05 and 0.3 μm.

Another object of the present invention is the production of a paint comprising the glossing/opacifying coating composition of the invention.

Examples of Glossing/Opacifying Coating Compositions

Suspension or Dispersion Solids Content (% Equivalent Dry Weight)

The weight of the solid material in a suspension or dispersion is determined by weighing the solid material obtained by evaporating the aqueous phase of suspension and drying the obtained material to a constant weight.

Particle Size Distribution (Mass % Particles with a Diameter<X) and Median Grain Diameter ($d_{50}$ (Sedi), $d_{50}$ (Mal) and $d_{98}$ (Mal)) of Particulate Material Weight median grain diameter ($d_{50}$ (Sedi)) and grain diameter mass distribution of a particulate material are determined via the sedimentation method, i.e. an analysis of sedimentation behavior in a gravimetric field. The measurement is made with a Sedigraph™ 5100.

The method and the instrument are known to the skilled person and are commonly used to determine grain size of fillers and pigments. The measurement is carried out in an aqueous solution of 0.1% by weight of $Na_4P_2O_7$. The samples were dispersed using a high-speed stirrer and ultrasonic means.

Weight median grain diameter ($d_{50}$ (Mal)) was evaluated using a Malvern Mastersizer 2000 (Frauenhofer). The $d_{98}$ (Mal) value, measured using a Malvern Mastersizer 2000 (Frauenhofer), indicates a diameter value such that 98% by weight of the particles have a diameter of less than this value.

BET Specific Surface Area ($m^2$/g)

BET specific surface area values were determined using nitrogen and the BET method according to ISO 9277.

Gloss of a Coated Surface

Gloss values are measured at the listed angles according to DIN 67 530 on painted surfaces prepared with a coater gap of 150 and 300 μm on contrast cards.

Contrast Ratio (Opacity) of a Coated Surface

Contrast ratio values are determined according to ISO 6504/3 at a spreading rate of 7.5 m²/l.

Suspension or Dispersion Brookfield-Viscosity (mPas)

Brookfield-viscosities are measured with a Brookfield DV-II Viscometer equipped with a LV-3 spindle at a speed of 100 rpm and room temperature (20±3° C.).

Pigment Volume Concentration (PVC, %)

The pigment volume concentration is calculated as described in Section 6.2.3 of the book entitled "Fuellstoff" by Detlef Gysau (Hannover: Vincentz Network 2005).

$$\frac{\text{Total sum by volume of all pigments} + \text{extenders in paint}}{\text{Total sum by volume of all solid ingredients in paint}} \times 100\%$$

Critical Pigment Volume Concentration (CPVC, %)

The critical pigment volume concentration is a well known concentration widely used in the paint industry. It is generally considered to represent the point at which there is just enough resin to wet the pigment particles, and changes to the PVC near to the CPVC can result in abrupt changes to coating properties, such as porosity and gloss. The CPVC and its measurement method according to ISO 4618 are discussed in Section 6.2.4 of the book entitled "Fuellstoff" by Detlef Gysau (Hannover: Vincentz Network 2005).

Materials:

SMGCC

SMGCC dispersions used in the following examples are natural ground calcium carbonate (marble from Vermont) having the median particle size $d_{50}$ and particle size characteristics given in the table below.

TABLE 4

| SMGCC | Solids (%) | SSA (m²/g) | % <1 μm | % <0.5 μm | % <0.2 μm | $d_{98}$ (Mal) μm | $d_{50}$ (Mal) μm | $d_{98}/d_{50}$ (Mal) |
|---|---|---|---|---|---|---|---|---|
| 1 | 60 | 36.0 | 98.3 | 94.3 | 65.1 | 0.53 | 0.62 | 5 |
| 2 | 49 | 37.7 | 98.3 | 94.8 | 65.7 | 0.55 | 0.122 | 4.5 |
| 3 | 46 | 38.6 | 97.7 | 94.8 | 69.5 | 0.31 | 0.128 | 2.4 |

Titanium Dioxide

The titanium dioxide employed in the examples herebelow consists of 95% by weight of pure rutile $TiO_2$, with the remaining weight being accounted for in a surface treatment of alumina, zirconia and an organic surface treatment agent. This pigment features a d50 (Mal) of approximately 0.55 μm and is provided in the form of an aqueous paste having a 75% solids content. By scanning electron microscope imaging, the particles appear to be in the range of 0.2 to 0.25 μm. The refractive index of $TiO_2$ is 2.7.

Example 21

The following example illustrates a comparative paint composition and paint compositions according to the invention. The formulated paints were applied to a contrast card in the necessary amounts in order to measure both gloss and opacity.

TABLE 5

| | Example | | | |
|---|---|---|---|---|
| | 1 | 2 | 3 | 4 |
| | Comparison (CO)/Invention (IN) | | | |
| | CO | IN | IN | IN |
| Paint composition formulation | | | | |
| Water (g) | 133.6 | 119.8 | 110.9 | 108.0 |
| Hydrophilic copolymer dispersant, 50% solids content (g) | 6.4 | 6.5 | 6.5 | 6.5 |
| Ammonia, 24% active content (g) | 4 | 4 | 4 | 4 |
| Paraffin-based mineral oil mixture containing silicone (g) | 7 | 7 | 7 | 7 |
| Rheotech 200 thickener from Coatex (g) | 15 | 15 | 15 | 15 |
| Propylene glycol (g) | 10 | 10 | 10 | 10 |
| Butyl diglycol (g) | 5 | 5 | 5 | 5 |
| Dipropylene Glycol n-Butyl Ether (g) | 10 | 10 | 10 | 10 |
| Ester alcohol with Mw = 216 g/mol (g) | 9 | 9.11 | 9.11 | 9.11 |

TABLE 5-continued

| | Example | | | |
|---|---|---|---|---|
| | 1 | 2 | 3 | 4 |
| | Comparison (CO)/Invention (IN) | | | |
| | CO | IN | IN | IN |
| Acrylate binder emulsion, 48% active content (g) | 550 | 557 | 557 | 557 |
| $TiO_2$ (g) | 250 | 218 | 218 | 218 |
| SMGCC1 (g) | | 39 | | |
| SMGCC2 (g) | | | 48 | |
| SMGCC3 (g) | | | | 51 |
| % weight $TiO_2$ replaced by SMGCC | 0 | 12 | 12 | 12 |
| PVC (%), approx. | 21.1 | 21.1 | 21.1 | 21.1 |

TABLE 5-continued

| | Example | | | |
|---|---|---|---|---|
| | 1 | 2 | 3 | 4 |
| | Comparison (CO)/Invention (IN) | | | |
| | CO | IN | IN | IN |
| Properties on application of the paint formulation Contrast ratio at 7.5 m2/l spreading rate | | | | |
| (%) | 98.6 | 98.5 | 98.6 | 98.5 |
| Gloss obtained using a coater gap of 150 μm | | | | |
| 20° | 51.8 | 50.6 | 50.6 | 55.7 |
| 60° | 80.3 | 79.7 | 79.7 | 81.7 |
| 85° | 93.6 | 95.9 | 96.2 | 96.8 |
| Gloss obtained using a coater gap of 150 μm | | | | |
| 20° | 55.6 | 52.4 | 54.7 | 56.8 |
| 60° | 79.4 | 78.7 | 80.1 | 80.5 |
| 85° | 95.6 | 95.7 | 96.5 | 95.8 |

The results set forth in table 5 above demonstrate that replacing a part of $TiO_2$ with the SMGCC according to the invention, and having d98/d50 values ranging from 2.4 to 5, results in coatings having essentially the same opacity (contrast ratio) as the comparison formulation having equal PVC but only $TiO_2$. Gloss values are observed to be equivalent or improved relative to the comparison formulation having equal PVC but only $TiO_2$.

The invention claimed is:

1. A glossing and opacifying coating composition comprising an aqueous nanoparticle dispersion and at least one binder, wherein the nanoparticles have at least one of three dimensions that are less than 250 nm ($D_{90}$) (Mal) that are substantially dispersed in the at least one binder and have a mean particle size $D_{50}$ (Mal) of less than 1 micron, wherein the nanoparticles comprise ground calcium carbonate, wherein the at least one binder is selected from the group consisting of vinyl-acrylic, styrene-acrylic, acrylic dispersions, solution acrylics, polyurethanes dispersed either in water or solvent, polymers containing ester groups including polyesters, polyester-based polyurethanes, polyester-based polyureas and polyester-based polyamides and wherein the composition includes at least one pigment having a refractive index greater than or equal to 2.5.

2. The glossing and opacifying coating composition according to claim 1, wherein the nanoparticles have a mean particle size $D_{50}$ (Mal) of less than 500 nm.

3. The glossing and opacifying coating composition according to claim 1, wherein the nanoparticles have a mean particle size $D_{50}$ (Mal) of less than 100 nm.

4. The glossing and opacifying coating composition according to claim 1, wherein the nanoparticles have a mean particle size $D_{50}$ (Mal) of less than 50 nm.

5. The glossing and opacifying coating composition according to claim 1, wherein the nanoparticles have a particle size $D_{90}$ (Mal) of less than 100 nm.

6. The glossing and opacifying coating composition according to claim 1, wherein the nanoparticles have a particle size $D_{90}$ (Mal) of less than 50 nm.

7. The glossing and opacifying coating composition according to claim 1, wherein the nanoparticles have a nitrogen BET surface area of greater than 20 $m^2/g$.

8. The glossing and opacifying coating composition according to claim 1, wherein the nanoparticles have a nitrogen BET surface area of greater than 30 $m^2/g$.

9. The glossing and opacifying coating composition according to claim 1, wherein the nanoparticles have a nitrogen BET surface area of greater than 35 $m^2/g$.

10. The glossing and opacifying coating composition according to claim 1, wherein the nanoparticles have a nitrogen BET surface area of greater than 40 $m^2/g$.

11. The glossing and opacifying coating composition according to claim 1, wherein the nanoparticles are ground calcium carbonate obtained from one or more of chalk, limestone and marble.

12. The glossing and opacifying coating composition according to claim 1, wherein the nanoparticles are submicron ground calcium carbonate (SMGCC).

13. The glossing and opacifying coating composition according to claim 1, wherein the nanoparticles are dispersed in a polyester-polyurethane polymer binder.

14. The glossing and opacifying composition according to claim 1, having a pigment volume concentration (PVC) of from 5% up to the critical pigment volume concentration (CPVC) and comprising at least one ground calcium carbonate having a $D_{50}$ (Mal) of between 0.05 and 0.3 μm.

15. The glossing and opacifying composition according to claim 14, wherein the ground calcium carbonate has a $D_{50}$ (Mal) of between 0.1 and 0.3 μm.

16. The glossing and opacifying composition according to claim 14, wherein the ground calcium carbonate has a $D_{98}/D_{50}$ (Mal) of greater than 3.

17. The glossing and opacifying composition according to claim 14, wherein the ground calcium carbonate has a $D_{98}$ (Mal) of less than or equal to 1 μm.

18. The glossing and opacifying composition according to claim 14, wherein the ground calcium carbonate has a $D_{98}$ (Mal) of less than or equal to 0.6 μm.

19. The glossing and opacifying composition according to claim 14, wherein the ground calcium carbonate has a $D_{98}$ (Mal) of less than or equal to 0.4 μm.

20. The glossing and opacifying composition according to claim 1, wherein the ground calcium carbonate has a refraction index of approximately 1.5 to 1.7.

21. The glossing and opacifying composition according to claim 1, wherein the pigment having a refractive index of greater than or equal 2.5 is one or more of titanium dioxide, zinc sulphide and zinc oxide.

22. The glossing and opacifying composition according to claim 21, wherein the pigment having a refractive index of greater than or equal 2.5 is titanium dioxide.

23. The glossing and opacifying composition according to claim 22, wherein a titanium dioxide:ground calcium carbonate weight ratio is of 70:30 to 98:2.

24. The glossing and opacifying composition according to claim 22, wherein a titanium dioxide:ground calcium carbonate weight ratio is of 85:15 to 90:10.

25. A method of forming the glossing and opacifying composition of claim 1, wherein the ground calcium carbonate is mixed with the at least one pigment and the at least one binder.

26. A substrate comprising or coated with the glossing and opacifying composition according to claim 1.

27. The coated substrate according to claim 26, wherein the substrate is selected from the group consisting of porous and non-porous substrates, papers, non-woven materials, textiles, leather, wood, concrete, masonry, metals, house wrap, building materials, fiberglass, polymeric articles, personal protective equipment, carpets, textiles used in clothing, upholstery, tents, awnings, air bags, fabrics, yarns, and blends, whether woven, non-woven, or knitted, and whether natural, synthetic, or regenerated.

28. The coated substrate according to claim 26, wherein the substrate is selected from the group consisting of papers, non-wovens, fibrous materials, films, sheets, composites inks, printing binders, flock and other adhesives, personal hair products, skin care products, hair care products, nail care products, livestock and feed applications.

29. The coated substrate according to claim 26, wherein the coating composition is applied to the substrate in an amount so as to form a layer having a thickness of between 100 and 400 nm.

30. The coated substrate according to claim 26, wherein the glossing and opacifying coating composition provides a gloss measured at 60° of greater than 70% and an opacity of greater than 97%.

31. A method of forming a coated substrate coated with a glossing and opacifying composition comprising applying the glossing and opacifying composition of claim 1 to coat the substrate.

32. The method according to claim 31, wherein the coating composition is applied to the substrate in an amount so as to form a layer having a thickness of between 100 and 400 nm.

33. The method according to claim 31, wherein the coated substrate is further dried and optionally cured.

* * * * *